United States Patent [19]

Mori

[11] Patent Number: 4,555,864
[45] Date of Patent: Dec. 3, 1985

[54] CHLORELLA NURTURING DEVICE

[76] Inventor: Kei Mori, 3-16-3-501, Kaminoge, Setagaya-ku, Tokyo, Japan

[21] Appl. No.: 620,406

[22] Filed: Jun. 14, 1984

[30] Foreign Application Priority Data

Jun. 24, 1983 [JP] Japan .................................. 58-114768

[51] Int. Cl.⁴ ............................................... A01G 7/00
[52] U.S. Cl. ....................................... 47/1.4; 126/439; 126/440
[58] Field of Search .......................... 126/436, 438–440, 126/424, 425, 437; 350/96.10, 96.18; 47/1.4

[56] References Cited

U.S. PATENT DOCUMENTS 4,195,620 4/1980 Rust ....................................... 126/439
4,434,787 3/1984 Young, II ............................. 126/440

FOREIGN PATENT DOCUMENTS 2384216 11/1978 France .................................. 126/440
61542 5/1981 Japan .................................... 126/440

*Primary Examiner*—James C. Yeung
*Attorney, Agent, or Firm*—Jordan and Hamburg

[57] ABSTRACT

A chlorella nurturing device comprises a chlorella nurturing tank constructed with a transparent material on the upper surface thereof and a reflection mirror assembly for reflecting downward vertically solar rays. The solar rays are reflected on the reflection mirror and guided into the chlorella nurturing tank through the transparent material at the upper surface thereof. The reflection mirror is constructed with a large number of dual-surface reflection mirror plates unitarily arranged in parallel in a south-north direction.

8 Claims, 5 Drawing Figures

4,555,864

CHLORELLA NURTURING DEVICE

BACKGROUND OF THE INVENTION

The present invention relates to a chlorella nurturing device, particularly, a chlorella nurturing device which can preferably be used at a place near the equator.

The present applicant has previously proposed various kinds of chlorella nurturing devices effectively utilizing solar rays. However, those proposals were performed only in consideration of their application to buildings or the like. The conventional chlorella nurturing device employed artificial light in an effective combination with solar rays. Such use was limited to highly advanced countries where artificial light sources could easily be obtained. Therefore, in order to nurture chlorella in a most primitive way, it was necessary to make an artificial pond and only to utilize solar rays. However, in the case of nurturing chlorella in an artificial pond, all of the solar rays are normally reflected on the upper surface of the water at an incidence angle of about 45° or less, so that no rays enter the pond. For this reason, the efficiency of producing chlorella in this way is very low.

However, one would think that if such a method of nurturing chlorella in an artificial pond was applied to a place nearer to the equator which received an abundance of direct solar rays, its efficiency might be greatly increased. However, there exist many birds and insects in those equatorial areas and consequently an artificial pond would be polluted by those living things. Furthermore, the pond sometimes overflows its banks because of storms, or the nurtured chlorella becomes diluted unexpectedly. Until now, such problems could not be dealt with.

SUMMARY OF THE INVENTION

It is therefore an object of the present invention to provide a chlorella nurturing device which can be preferably used at a place near the equator.

It is another object of the present invention to provide a chlorella nurturing device which is simple in construction and inexpensive.

A chlorella nurturing device is comprised of a chlorella nurturing tank constructed with a transparent material on the upper surface thereof and a reflection mirror assembly for reflecting solar rays downwardly. The solar rays reflected by the reflection mirror guided into the chlorella nurturing tank through the transparent material at the upper surface thereof. The reflection mirror is constructed with a large number of dual-surfaces reflection mirror plates unitarily arranged in parallel in a south-north direction. A large number of optical conductors are installed in the chlorella nurturing tank in such a manner that they project outside through the transparent material at the upper surface of the tank.

The above-mentioned and other objects, features and advantages of the present invention will become apparent from the following detailed description accompanied by drawings.

DESCRIPTION OF THE PREFERRED EMBODIMENT

Figure 1:
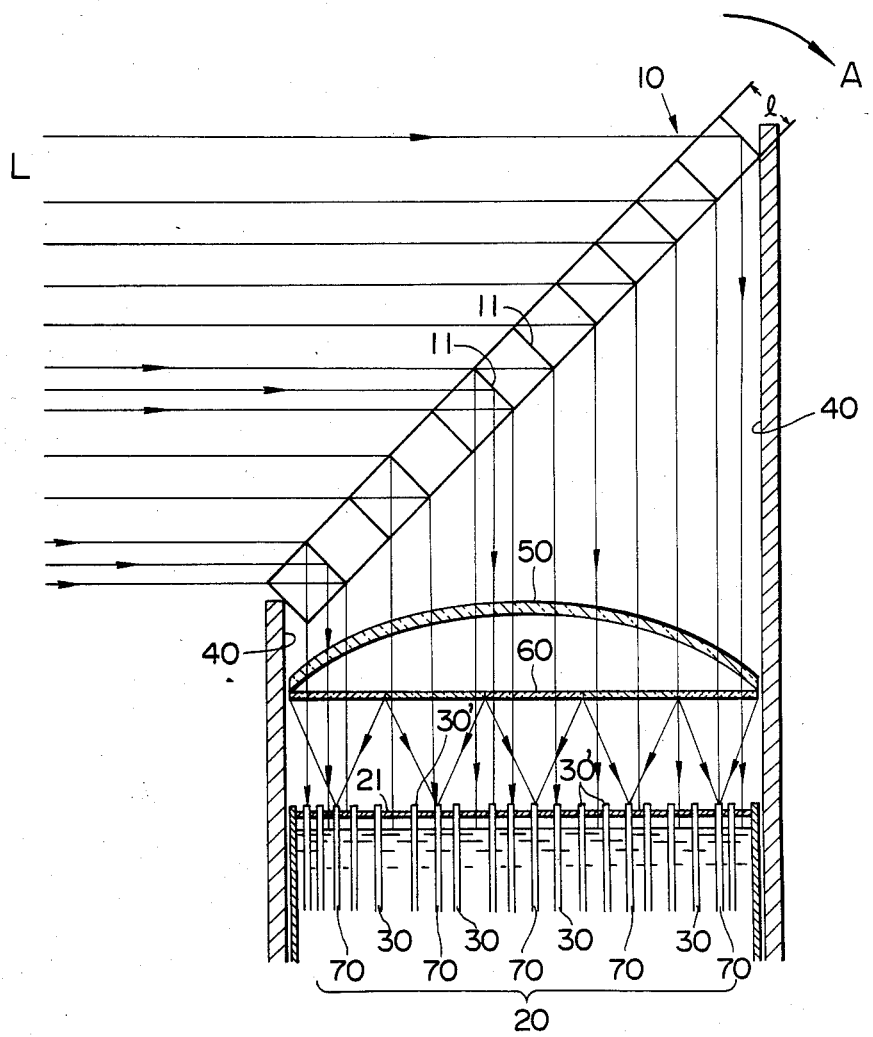
FIGS. 1 through 3 are explanatory views illustrating the construction of a chlorella nurturing device according to one embodiment of the present invention.
Figure 2:
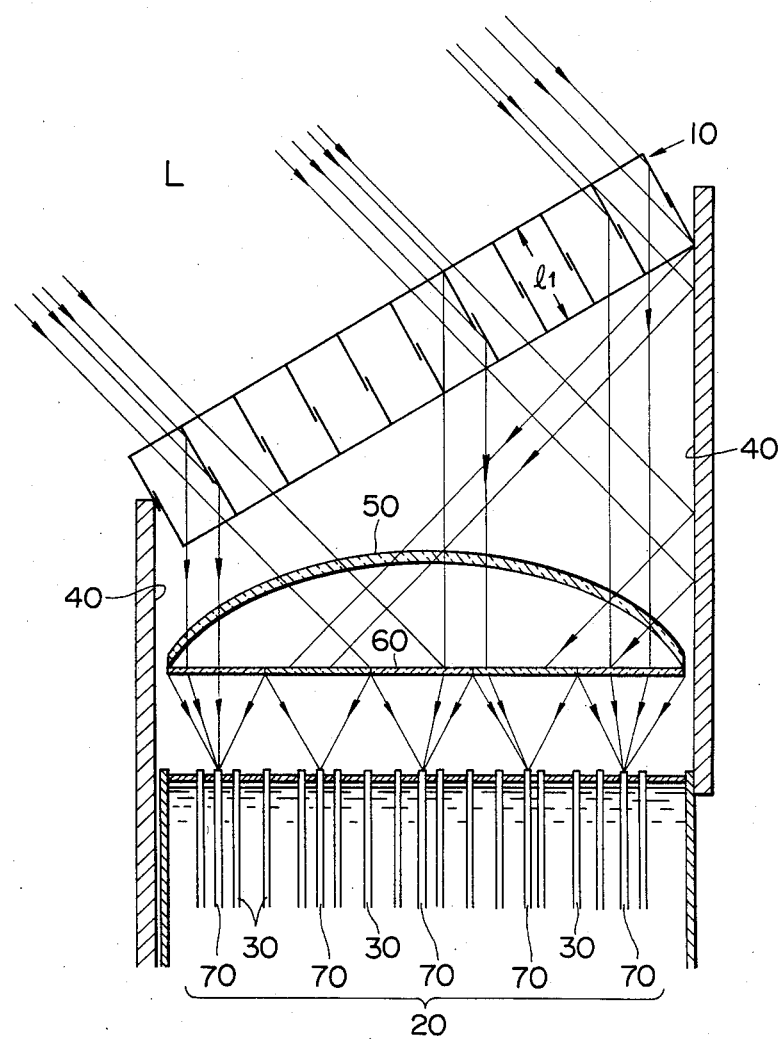
Figure 3:
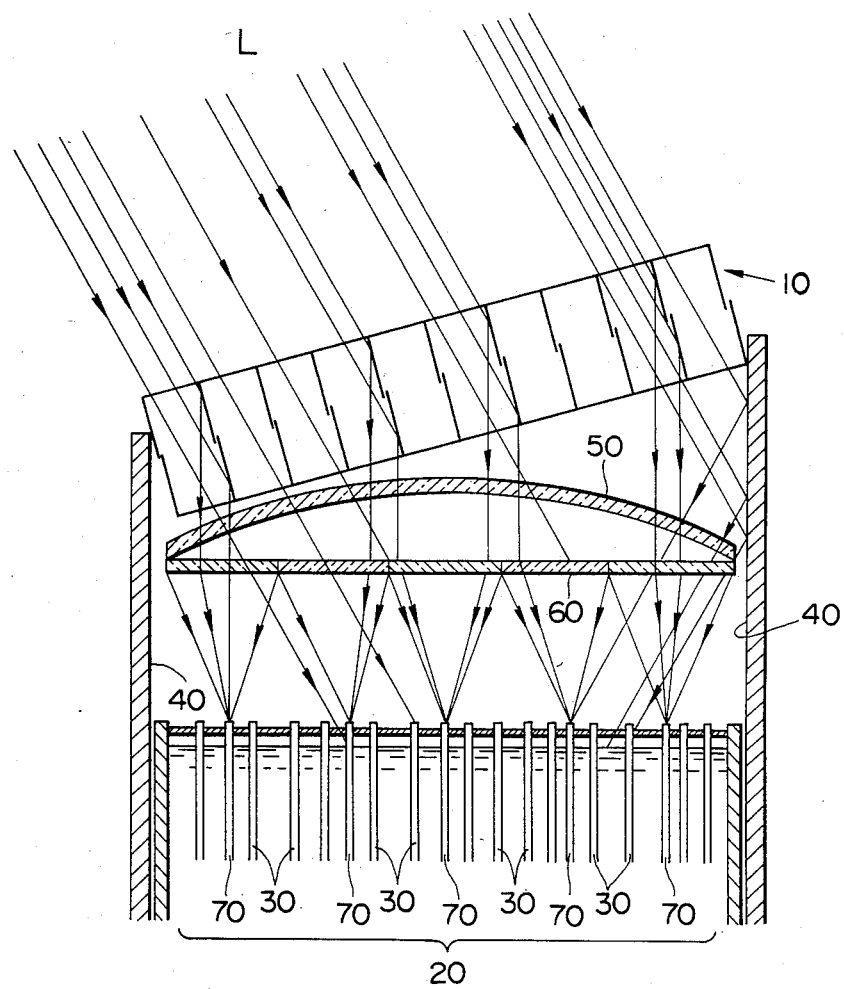

FIGS. 1 through 3 are explanatory views illustrating the main construction part of a chlorella nurturing device according to one embodiment of the present invention. In the Figures, 10 is a reflection mirror assembly and 20 is a chlorella nurturing tank. FIG. 1 shows the condition at the time of sunrise (or sunset); FIG. 2 shows the condition at 9 o'clock in the morning (or at 3 o'clock in the afternoon); and FIG. 3 shows the condition at 10:30 in the morning (or at 1:30 in the afternoon).

Inside the reflection mirror assembly 10, a large number of dual-surface reflection mirror plates 11 are installed in parallel, being elongated along a south-north direction. As shown in the Figures, when the solar ray L reaches the aforementioned mirror plate 11, it is reflected by plate 11 and directed downwardly (vertically).

On the other hand, at least the upper end portion 21 of the chlorella nurturing tank 20 is constructed with a transparent material. The solar rays reflected by the reflection mirror assembly 10 are guided into the chlorella nurturing tank 20 through the transparent portion 21. However, in such conditions, the intensity of the light at the upper level of the chlorella nurturing tank may be too strong so that chlorella nurturing at the upper level may not be performed effectively, and a sufficient amount of solar rays may not reach the lower layer portions of the tank. The efficiency of chlorella nurturing is impeded thereby.

Optical conductors 30 are installed for avoiding such an occurrence. The light-receiving edges 30' of the respective optical conductors 30 project outside through the upper surface (the upper cover) 21 of the chlorella nurturing tank. As mentioned above, a portion of the solar rays reflected by the reflection mirror assembly 10 are guided into the optical conductors 30, and further transmitted onto the lower portion of the chlorella nurturing tank through the optical conductors 30. Consequently, the intensity of the light may be weakened at the upper layer of the chlorella nurturing tank 20 while the intensity of the light at the lower levels may be strengthened so that the intensity of light becomes approximately uniform throughout, and the efficiency of chlorella nurturing is greatly improved.

As time goes by, the sun rises upward and the incidence angle of the solar rays becomes gradually wider and wider as shown in FIGS. 2 and 3. The reflection mirror assembly 10 is rotatably moved in the direction shown by Arrow A corresponding to the incidence angle of the solar rays. In such a manner, the solar rays reflected by the reflection mirror plate 11 are always so controlled as to direct them downwardly (vertically). Supposing that the length l of the reflection mirror plate is then kept constant and a part of the solar ray bundles passes through the reflection mirror plate 11 so that the efficiency of the solar ray utilization is weakened. In order to settle such problems, the length l of the reflection mirror is enlarged to l'. The amount of the light directed downwardly (vertically) increases in proportion to the increase of the length thereof so that the solar rays can be more effectively utilized.

Figure 4A:
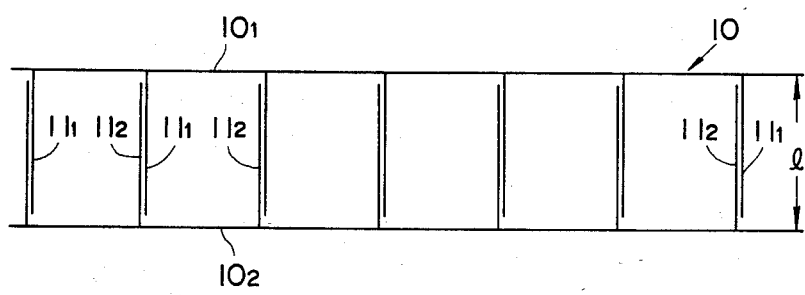
FIGS. 4(a) and 4(b) are explanatory views for illustrating an example of a reflection mirror which can be preferably used for practicing the present invention.
Figure 4B:
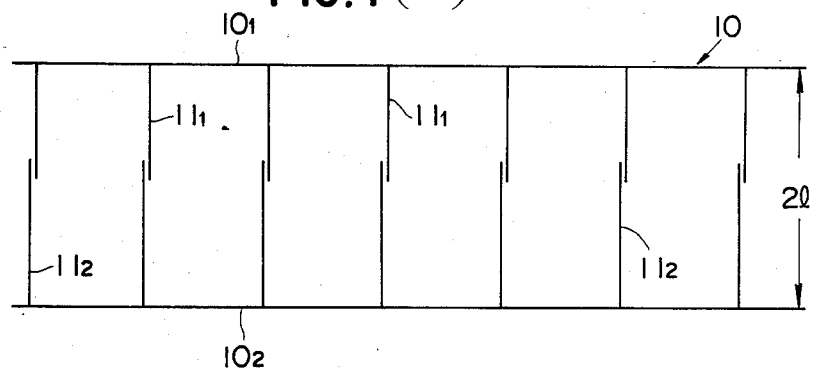

FIGS. 4(a) and 4(b) show an example of changing the length of the reflection mirror plate as shown before. In FIGS. 4(a) and 4(b) $10_1$ and $10_2$ are reflection mirror components constituting the aforementioned reflection mirror assembly 10, and $11_1$ and $11_2$ are dual-surface reflection mirror plates installed respectively on the corresponding reflection mirror components $10_1$ and $10_2$. A pair of such reflection mirror components $10_1$ and $10_2$ are tightly attached to each other as shown in FIG. 4(a) and 4(b). When the solar rays go forward horizontally both of the dual-surface reflection mirror plates $11_1$ and $11_2$ are completely engaged with each other and the length thereof becomes l as shown in FIG. 4 (a). When the sun rises, both mirror plates are disengaged and then the total length of both mirror plates becomes 2l, the maximum length possible, as shown in FIG. 4 (b).

Nevertheless, a part of the solar ray bundles passes through into the reflection mirror plate. On such an occasion, reflection mirrors 40 are installed along the side walls of the chlorella nurturing tank, and each end of the reflection mirror 40 is elongated upward. In such a way, the solar rays passing between the reflection mirror are reflected by the reflection mirror 40 and transmitted back onto the upper surface of the chlorella nurturing tank 20.

Moreover, since the solar rays go forward from directly above at noon, they pass the reflection mirror assembly 10 without being stopped and are utilized by the chlorella nurturing tank 20. In the afternoon, utilizing the opposite reflection surface of the reflection mirror plate 11, the solar rays are guided into the chlorella nurturing tank in the reverse order. In such a manner, according to the present invention, the chlorella nurturing liquid in the tank may not be polluted by the droppings of birds, insect's ala, etc, because the chlorella is nurtured inside the tank. Furthermore, since the chlorella nurturing device is not effected by scum it may always nurture chlorella consistently. Furthermore, in the case of nurturing the chlorella in the pond without using a reflection mirror assembly, according to the present invention, almost all of the solar ray bundles are reflected on the surface of a pond near the equator until 9 o'clock in the morning and after 3 o'clock in the afternoon so that those solar rays cannot be utilized in the process. However, according to the present invention, solar rays can be effectively utilized all day long.

The device of the present invention function as described above. The light-receiving edge 30' of the optical conductor 30 projects up from the upper surface of the chlorella nurturing tank 20. The surface tends to become easily dirty with dust, dirt, etc. and it is troublesome to clean the dirty portion thereof. Consequently its efficiency decreases. In order to avoid such a drawback a transparent cover 50 is installed over the upper surface of the chlorella nurturing tank. In such a manner the inconveniences mentioned can be easily eliminated.

On that occasion, a lens 60 is installed under the cover 50, the solar rays are focused by the lens 60, and the focused solar rays are guided in to an optical conductor 70 and further guided onto the lower portion of the chlorella nurturing tank through the optical conductor 70. By using such a design the intensity of the light at the upper layer of the chlorella nurturing tank is further weakened while the intensity of the light at the lower portion thereof is further strengthened. In such a manner it may be possible to nurture the chlorella more and more effectively.

On that occasion, if the light-receiving edge of the optical conductor 30 is installed at a place near the optical conductor 70, the light, that is not guided into the optical conductor 70 among the solar ray bundles focused by the lens 60 is likely to be guided into the optical conductor 30. Thereby, it may be possible to guide the solar rays more efficiently into the chlorella nurturing tank.

The chlorella nurturing device according to the present invention is illustrated heretofore in the case of employing the device at a place near the equator. However, it is possible to employ this device at other high-latitude places besides the equator. On those occasions, if the reflection mirror assembly 10 is rotatably moved not only in an east-west direction as mentioned above but also in a south-north direction, the solar rays can be guided into the chlorella nurturing tank without decreasing its efficiency.

As is apparent from the foregoing description, it may be possible to produce a chlorella nurturing device which is simple in construction and inexpensive, and that can be effectively employed at a place near the equator.

What is claimed is:

1. A chlorella nurturing device comprising a chlorella nurturing tank containing a chlorella nurturing liquid, optical conductor means disposed within said tank, said optical conductor means comprising a plurality of elongated optical conductor members extending into said liquid and having upper end portions extending above the upper surface of said liquid, reflection mirror means disposed over said tank for reflecting solar rays generally downwardly into said tank, a plurality of lenses disposed between said reflector means and said optical conductor means, each of said conductor members having a light-receiving edge on said upper end portion thereof, said conductor members being disposed so that said light-receiving edges are positioned at the focus of each of said lenses such that solar rays focused by said lenses are guided into said conductor members and thus further guided into said liquid below the upper surface thereof, whereby the intensity of the solar light at the upper levels of said chlorella nurturing liquid is weakened while the intensity of the solar light at the lower levels is strengthened to thereby enhance uniformity of light intensity in said chlorella nurturing liquid.

2. A chlorella nurturing device according to claim 1, wherein said optical conductor means further comprises a transparent material disposed above the level of said liquid, said solar rays reflected by said reflection mirror means passing through said transparent material onto the upper surface of said liquid.

3. A chlorella nurturing device according to claim 2, wherein said upper end portions of said conductor members pass through and extend above said transparent material.

4. A chlorella nurturing device according to claim 1, wherein said reflection mirror means comprises a plurality of dual-surface surface mirror plates constructed to provide for adjusting the length of said dual-surface mirror plates.

5. A chlorella nurturing device according to claim 4, wherein said dual-surface mirror plates are disposed in parallel array in a south-north direction.

6. A chlorella nurturning device according to claim 1 further comprising a transparent cover disposed below said reflection mirror means.

7. A chlorella nurturing device according to claim 1 further comprising reflection means located along the inner side walls of said tank.

8. A chlorella nurturing device comprising a chlorella nurturing tank containing a chlorella nurturing liquid, a transparent material disposed above the level of said liquid, elongated optical conductors disposed within said tank, said optical conductors extending into said said liquid and having upper end portions extending above said liquid and through said transparent material, reflection mirror means disposed over said tank for reflecting solar rays generally downwardly into said tank, a plurality of lenses disposed between said reflector means and said optical conductors, each of said optical conductors having a light-receiving edge on said upper end portion thereof, said optical conductors being disposed so that said light-receiving edges are positioned at the focus of each of said lenses such that solar rays focused by said lenses are guided into said optical conductors and thus further guided into said liquid below the upper surface thereof, whereby the intensity of the solar light at the upper levels of said chlorella nurturing liquid is weakened while the intensity of the solar light at lower levels is strengthened to thereby enhance uniformity of light intensity in said chlorella nurturing liquid.

* * * * *